US00PP21859P2

(12) United States Plant Patent
Egger

(10) Patent No.: US PP21,859 P2
(45) Date of Patent: Apr. 5, 2011

(54) ***HEUCHERA* PLANT NAMED 'SHANGHAI'**

(50) Latin Name: ***Heuchera* hybrid**
Varietal Denomination: Shanghai

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 36 days.

(21) Appl. No.: 12/653,617

(22) Filed: Dec. 14, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner* — Kent L Bell
(74) *Attorney, Agent, or Firm* — Klarquist Sparkman, LLP

(57) ABSTRACT

A new and distinct *Heuchera* plant characterized by small veiled purple leaves year round, very free flowering medium to short flower stalks, ivory colored flowers on purple black peduncles, repeat blooming, a well branched, small, mounding habit, and excellent vigor.

1 Drawing Sheet

Botanical denomination: *Heuchera* hybrid.
Variety designation: 'Shanghai'.

BACKGROUND OF THE INVENTION

The present invention relates to a new and distinct cultivar of *Heuchera* and given the cultivar name of 'Shanghai'. *Heuchera* is in the family Saxifragaceae. *Heuchera* 'Shanghai' originated from a cross between *Heuchera* 766-5, a proprietary non-commercial hybrid, as the seed parent, and *Heuchera* 758-1, a proprietary non-commercial hybrid, as, as the pollen parent.

Compared to the seed parent, *Heuchera* 766-5, the new cultivar has smaller leaf size, ivory rather than light pink to white flowers.

Compared to the pollen parent, *Heuchera* 758-1, the new cultivar has ivory rather than pink flowers, and smaller leaves.

Compared to *Heuchera* 'Ebony & Ivory' (U.S. Plant Pat. No. 11,380), the new cultivar has a smaller habit, smaller leaves, and a purple leaf color rather than dark.

This new *Heuchera* is uniquely distinguished by:

1. small veiled purple leaves year round,
2. very free flowering on medium to short flower stalks,
3. ivory colored flowers on purple black peduncles,
4. repeat blooming,
5. well branched, small, mounding habit,
6. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The photo shows a 10-month-old plant of *Heuchera* 'Shanghai' growing in the ground in full sun in the garden in August in Canby, Oreg.

DETAILED PLANT DESCRIPTION

The following is a detailed description of the new *Heuchera* cultivar based on observations taken in April of one-year-old specimens growing in a one gallon container outside in full sun in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart, 1999 edition, except for spring leaf color which uses the 5$^{th}$ edition.

Plant:

*Form.*—Basal rosette, herbaceous perennial.
*Hardiness.*—USDA Zone 4 to 9.
*Size.*—18 cm tall from top of the foliage to the ground and 34 cm wide.
*Habit.*—Mounding.
*Vigor.*—Excellent.

Leaf:

*Type.*—Simple.
*Arrangement.*—Rosette.
*Shape.*—Broadly ovate to orbicular.
*Lobing/division.*—5 to 7 shallow lobes, the terminal the longest, shallow secondary lobes.
*Venation.*—Palmate.
*Margins.*—Broadly crenate.
*Apex.*—Mucronulate.
*Base.*—Cordate, lobes overlapping slightly at the base.
*Blade size.*—Grows to 8.5 cm long and 7.3 cm wide.
*Texture.*—Leathery.
*Surface texture.*—Glabrous on the top and glandular on the bottom.
*Petiole description.*—Grows to 10.5 cm long and 2 mm wide, glandular hairs, closest to Grayed Purple 187B.

*Leaf color.*—Topside, spring leaves are Purple N79A with veins Greyed Purple N186A on top and Purple N77 on bottom side; mature summer thru winter leaves are between Gray 201A and 201B with the veins closest to Black 202A, immature summer to fall leaves are closest to Grayed Purple 187A, with leaf undersides Red Purple 59A.

Inflorescence:

*Size.*—Grows to 8 cm wide and 22 cm long.

*Type.*—Thyrse.

*Number of flowers per thyrse.*—About 100.

*Number of thyrse.*—About 18 in the first spring flush.

*Peduncle.*—About 50 cm long, 3 mm wide at base, Greyed Purple 187A, glandular hairs, usually with no cauline leaves.

*Pedicel.*—Variable in size, with glandular hairs, Greyed Purple 187A.

*Bloom period.*—April through November in Canby, Oreg.

Flower bud:

*Size.*—3 mm wide and 4 mm long.

*Description.*—Glandular puberulent, ovoid, down facing.

*Color.*—Greyed Yellow 161D with tips Yellow Green 148A and base Greyed Orange N167A.

Flower:

*Type.*—Perfect.

*Shape.*—Campanulate.

*Size.*—6 mm long and 6 mm wide.

*Corolla description.*—5 petals, 3 mm long and 1.5 mm wide, broadly spatulate, glandular on both sides, bottom half entire top half sparsely irregularly incised, White NN155C.

*Calyx description.*—Campanulate, 6 mm long and 6 mm wide, with 5 lobes divided ½ way to the base, each 3 mm wide and 3 mm long, glandular hairs outside and inside, tips obtuse, margin entire; Yellow White 158C with tips Greyed Green 189A and just below the tips the area is tinted Greyed Purple 185A, base Yellow Green 148A inside and out.

*Stamen description.*—5 in number, filaments 2 mm long, White NN155C, anthers sterile, 0.4 mm, Yellow White 158A.

*Pistil description.*—1, 2-beaked, 4.5 mm long; Green Yellow 1 C, ovary 2 mm long; style 2.5 mm long.

*Fragrance.*—None.

*Lastingness.*—Each thyrse blooms for about 3 weeks on the plant.

Fruit:

*Type.*—Two-beaked ovoid capsule.

*Fertility.*—Low.

*Color.*—Greyed Brown 199C.

Seed:

*Shape.*—Linear.

*Size.*—2 mm long.

*Color.*—Black 202A.

Pest and disease tolerance: Excellent disease resistance to powdery mildew, the common problem of *Heuchera*. Susceptible to *Heuchera* rust and root weevils.

I claim:

1. A new and distinct *Heuchera* plant as herein illustrated and described.

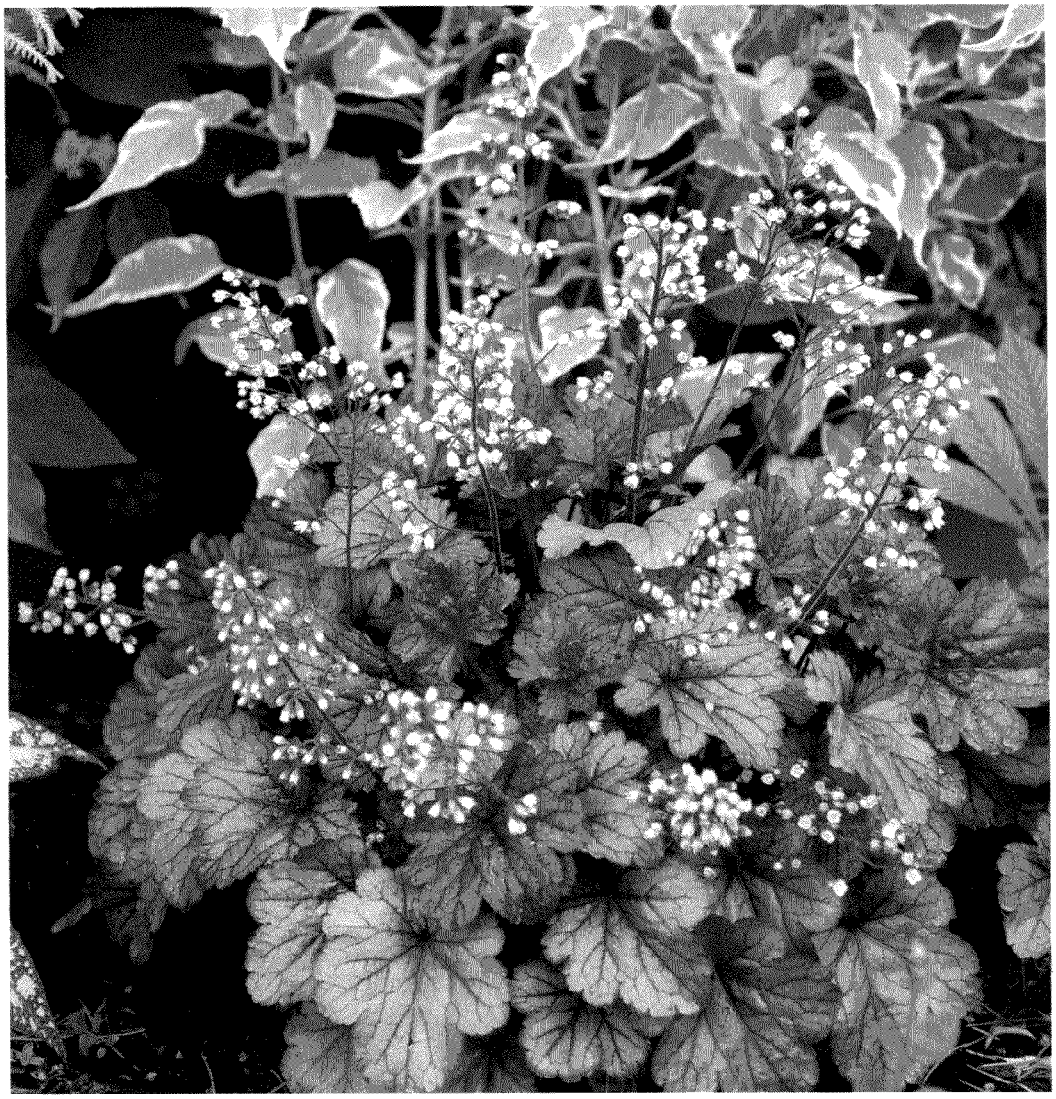

* * * * *